(12) United States Patent
Busch et al.

(10) Patent No.: US 8,026,483 B2
(45) Date of Patent: Sep. 27, 2011

(54) SPECTROSCOPIC DETERMINATION OF SUCROSE

(75) Inventors: Kenneth W. Busch, Waco, TX (US); Carlos Calleja-Amador, Waco, TX (US); Dennis H. Rabbe, Crawford, TX (US); Marianna Busch, Waco, TX (US)

(73) Assignee: Baylor University, Waco, TX (US)

(*) Notice: Subject to any disclaimer, the term of this patent is extended or adjusted under 35 U.S.C. 154(b) by 367 days.

(21) Appl. No.: 12/083,283

(22) PCT Filed: Oct. 11, 2006

(86) PCT No.: PCT/US2006/039036
§ 371 (c)(1),
(2), (4) Date: Mar. 20, 2009

(87) PCT Pub. No.: WO2007/044486
PCT Pub. Date: Apr. 19, 2007

(65) Prior Publication Data
US 2009/0201491 A1     Aug. 13, 2009

Related U.S. Application Data

(60) Provisional application No. 60/726,414, filed on Oct. 13, 2005.

(51) Int. Cl.
*G01N 21/21* (2006.01)
(52) U.S. Cl. ........... 250/338.1; 250/336.1; 250/372; 356/51; 356/432

(58) Field of Classification Search ............... 250/338.1; 356/51, 432; 702/22
See application file for complete search history.

(56) References Cited

FOREIGN PATENT DOCUMENTS

| EP | 1205753 A2 * | 5/2002 |
| EP | 1437086 A1 * | 7/2004 |
| WO | WO 03027645 A1 * | 4/2003 |
| WO | WO 2005057191 A1 * | 6/2005 |

OTHER PUBLICATIONS

Soyemi, O., et al; "Design of a Modular, Dispersive Spectrometer for Fundamental Studies in NIR Spectroscopy"; Spectroscopy, vol. 16, pp. 24-33, Apr. 2001.

* cited by examiner

*Primary Examiner* — David Porta
*Assistant Examiner* — Djura Malevic
(74) *Attorney, Agent, or Firm* — Jackson Walker L.L.P.

(57) ABSTRACT

A method for determining sugar concentration using spectropolarimetry and multivariate regression modeling A set of fixed polarizers are used in association with a spectrometer, which enables the measurement of optical rotation as absorbance values over a range of wavelengths. The adverse effects of color within the samples is corrected by measuring a background level of absorbance that is not due to optical rotation and using this as a baseline. A regression model is then developed for predicting sugar concentration in unknown samples. This method is effective even if the sample is colored.

7 Claims, 13 Drawing Sheets

SPECTROSCOPIC DETERMINATION OF SUCROSE

This application claims priority to U.S. Provisional Patent Application Ser. No. 60/726,414, entitled "SPECTROSCOPIC DETERMINATION OF SUCROSE" filed on Oct. 13, 2005, having K. Busch, C. Calleja-Amador, D. Rabbe and M. Busch, listed as the inventor(s), the entire content of which is hereby incorporated by reference.

BACKGROUND

This invention pertains to the determination of sucrose concentration using spectroscopy, polarimetry, and multivariate regression.

Enantiomers are mirror-image isomers that have identical chemical and physical properties, making them difficult to separate and quantify. They can be distinguished optically by means of linearly polarized light. Linearly polarized light is light whose electric vector is confined to a particular plane. When linearly polarized light is passed through a sample containing a chiral molecule, one member of the enantiomeric pair rotates the plane of polarized light in one direction while the other rotates the plane of polarized light in the opposite direction. If the enantiomer rotates the plane of polarized light in a clockwise direction (when viewed by looking back at the source), the enantiomer is referred to as being dextrorotatory. If the enantiomer rotates the plane of polarized light counter-clockwise, it is levorotatory. If the sample contains equal amounts of both enantiomers, it is referred to as being racemic and does not rotate the plane of polarized at all.

A polarimeter is a device used to measure the optical activity of a sample. Polarimeters are well known and consist of a light source, a pair of polarizers, and an eyepiece or detector to measure the intensity of the light.

The sugar industry is by far the largest user of polarimetry today. Since the optical rotation of a sugar solution is proportional to the concentration of the solution, polarimetry is used routinely in the sugar industry to determine the concentration of sugar solutions. Sugar, or sucrose, is conventionally determined by polarimetry with the Clerget method, which consists of observing the difference in optical rotation before and after inversion of the sucrose by hydrolysis to glucose and fructose. One problem with the routine use of polarimetry for determination of the concentration of sugar solutions is coloration of the solution with raw sugar samples. In the conventional method, using the sodium wavelength at 589 nm, clarification is needed with many colored sugar samples like those from dark cane, sorghum, and beet products. To get accurate results, colored solutions need to be decolorized before the optical rotation is measured. Clarification and decolorization are typically accomplished by addition of basic lead acetate. Decolorization with lead acetate creates an expensive chemical disposal problem. Recently, because of concerns over the pollution problems associated with lead acetate, polarimetric measurements in the near infrared region, at about 880 nm, are being used with cane juices after conventional filtration. In this region, the chromagenic centers that cause color do not absorb radiation, so the measurement is not affected by the remaining yellow-brown color. This approach requires a near-infrared ("NIR") polarimeter. While using NIR radiation gets around the color problem, optical rotation decreases with increasing wavelength, so some accuracy may be lost.

The use of a polarized photometric detector in high-performance liquid chromatographic measurement of enantiomeric purity has been described (Yamamoto et al., 1996). The polarizers used were of sheet polarizing metal, which limits the spectral range to about 400 to 700 nm. The use of near-infrared radiation was not mentioned. Furthermore, only a single wavelength was utilized in any given application, which prevents the use of multivariate regression analysis.

SUMMARY

In one aspect, the current method for determining sucrose concentrations involves using cross polarizers and spectroscopy to obtain spectral data for a series of sugar samples and using multivariate regression techniques to create a model for predicting sugar concentration of unknown samples.

When ordinary unpolarized light passes through a polarizer, like a Glan-Taylor prism, it becomes linearly polarized. When light is linearly polarized, the plane of the electric vector of the lightwave is restricted to a particular plane that depends on the orientation of the polarizer. Consider a second polarizing prism placed after the first. If this second polarizer is rotated, the intensity of light passing out of the assembly will vary as the second prism is rotated about its axis. When the planes of the two polarizers are coincident, the light intensity that passes through the combination will be a maximum. When the planes of the two polarizers are at 90°, the light intensity will be at a minimum. Ideally, no light will be transmitted when the polarizers are orthogonal. According to Malus' law, the intensity of the light passing through the pair of polarizers will vary as $\cos^2 b$, where b is the angle between the two polarizers.

If a polarimeter is arranged so that the two polarizers are at 90° to one another, then no light should pass through the second polarizer. If an optically active sample is placed between the two polarizers, it will rotate the plane of polarized light so that some light passes through the second polarizer (the analyzer). If the analyzer is rotated so that the light is once again extinguished (null condition), the angle by which the polarizer was rotated is the optical activity of that sample. The amount of rotation caused by a given sample is proportional to the concentration of the sample and the path length of the cell used. The determination of optical rotation can be accomplished manually by rotating the analyzer. Modern instruments use some form of modulation (like Faraday modulation) to accomplish the task electronically.

Any ordinary polarimeter generally makes measurements at a single fixed wavelength. Historically, polarimetric measurements were made at 589 nm, which is the wavelength of one component of the sodium doublet. This was due to the availability of sodium lamps, which emit this wavelength. By using an atomic line, all polarimetric measurements were made at the same wavelength and could be compared. Today, modern instruments often have a number of wavelengths available that can be used. A spectropolarimeter is a device that measures the optical rotation over a range of wavelengths. A plot of optical rotation versus wavelength is known as an optical rotatory dispersion curve. Use of multi-wavelength data can provide additional information about a sample.

If a sample is colored so that the intensity of light passing through it is reduced appreciably, ordinary polarimetry becomes problematic because it is difficult to discern the null condition. In the case of using polarimetry to determine sugars (a technique known as saccharimetry), the presence of color in sugar samples like cane sugar and beet sugar causes problems. To avoid the effect of colored solutions, lead subacetate is added as a decolorizer. Use of lead subacetate to decolorize sugar samples has become increasingly problematic because it is a pollutant that costs money for chemical waste disposal.

The current method utilizes spectropolarimetry and is advantageous because the preferred spectropolarimeter has no moving parts. The polarizers are fixed, and modulation is not necessary. In addition, solid state array detection provides wavelength coverage from 200-1100 nm and a stable wavelength axis. The optical rotation is encoded as absorbance, and easy background correction is possible to remove the absorption by any achiral sample components. The stable absorbance axis permits reliable detection of very small absorbance differences. A large sample compartment is preferred in order to accommodate long cells. Furthermore, the collection of multiwavelength data permits the use of multivariate regression modeling in calibration, which can reduce pixel-to-pixel noise. The current method is useful because it enables the determination of sucrose concentration without the need to remove colored components.

In the current method, the polarizers are maintained in a fixed position, and the increase or decrease of the light transmitted by the pair of crossed polarizers is used in place of the measuring the actual angle of rotation as is done with a conventional polarimeter. Thus when an optically active solution is placed in the instrument, the sample rotates the plane of polarization, which, in turn, changes the amount of light passing through the instrument. One potential problem with this arrangement is the presence of an achiral absorbing concomitant in the sample. In this case, the presence of the absorbing species will also change the light passing through the instrument, making it impossible to detect the absorbance change due to optical rotation. The current method actually uses that problem to its advantage.

It is well known that absorbances are additive. The current method shows that it is possible to subtract out the absorbance of an absorbing species, leaving only the absorbance due to the optical rotation. This completely avoids the color problem with sugars because the absorbance of the colored component is removed completely. This means that the current method is not constrained to the near-infrared region to avoid the problems associated with color. Since optical rotation increases as the wavelength decreases, the current method can use shorter wavelengths because it removes the effect of colored agents instrumentally.

Multivariate regression is widely known in many areas of chemistry and can serve as a particularly powerful computational tool for correlating spectral data with known compositional changes in a test set of samples. The basic objective of the method is to develop a mathematical model that relates two sets of variables to each other so that the independent or X-variables can be used to determine the dependent or Y-variable.

To avoid problems with colinearity in the data, all multivariate regression techniques require an orthogonal basis set or coordinate system on which to represent the data. To achieve this condition, modern regression techniques employ projection methods to obtain a series of variance-scaled eigenvectors that can serve as a new coordinate system for the data. This form of data decomposition assures an orthogonal coordinate system for the data. At the same time, it provides a way to reduce the dimensionality of the data because only the major eigenvectors are needed to represent the data. Finally, when the data are represented on the new coordinate system, new insight is often gained as new relationships that were formerly obscured in the old coordinate system are revealed.

Broadly, one aspect of the present invention involves a method for determining the concentration of sugar in an unknown sample, comprising the steps of:

(1) Preparing a series of known samples, each of the known samples comprising a sugar compound having a known concentration;

(2) Collecting background spectral data of the known samples by passing light of various wavelengths through a first polarizer, a second polarizer oriented at a 45 degree angle with respect to the first polarizer, and the known sample, and recording the resultant light intensity with a spectrometer to give the background spectral data;

(3) Collecting known spectral data of the known samples by passing light of the various wavelengths through the first polarizer, the known sample, and the second polarizer oriented at a 45 degree angle with respect to the first polarizer, and recording the resultant light intensity with the spectrometer to give the known spectral data;

(4) Adjusting the known spectral data by subtracting the background spectral data to give adjusted known spectral data;

(5) Performing a principal component analysis and a regression of the adjusted known spectral data for each of the known samples to create a regression model;

(6) Collecting unknown background spectral data of an unknown sample by passing light of the set of various wavelengths through a first polarizer, a second polarizer oriented at a 45 degree angle with respect to the first polarizer, and the unknown sample, and recording the resultant light intensity with a spectrometer to give the unknown background spectral data;

(7) Collecting unknown spectral data of the unknown sample by passing light of the set of various wavelengths through the first polarizer, the unknown sample, and the second polarizer oriented at a 45 degree angle with respect to the first polarizer, and recording the resultant light intensity with the spectrometer to give the unknown spectral data;

(8) Adjusting the unknown spectral data by subtracting the unknown background spectral data to give adjusted unknown spectral data; and (9) Inserting the adjusted unknown spectral data into the regression vector to allow calculation of the unknown sugar concentration in the unknown sample.

In preferred embodiments, the sugar is sucrose. The spectral data is preferably UV spectral data that includes wavelengths that fall within the near-infrared region of the electromagnetic spectrum.

DETAILED DESCRIPTION OF PREFERRED EMBODIMENTS

The present invention relates to the determination of sucrose concentration using spectropolarimetry and multivariate regression modeling. In particular, the present invention involves the collection of spectral data for a series of sugar samples using fixed, cross polarimeters, measuring optical rotation over a range of wavelengths, correcting for background absorbances, and creating a regression model to predict sugar concentration in unknown samples.

One aspect of the current method is the use of a spectropolarimeter to collect optical rotatory dispersion information for a series of sugar samples. The preferred spectropolarimeter is based on an ordinary UV-visible spectrophotometer that can measure absorbance and has preferably been modified to accommodate long pathlength cells. The device uses a solid-state array detector to detect a spectral range from 200-1100 nm, thus providing optical rotatory dispersion information. Because the instrument uses array detection, which does not involve mechanically rotating a grating, the wavelength axis is highly stable. Optical rotation is not measured directly but instead is observed in terms of absorbance. Since all measurements are made in absorbance, which is an additive property, corrections for colored samples can be easily accomplished without need for chemical pretreatment.

Figure 1:
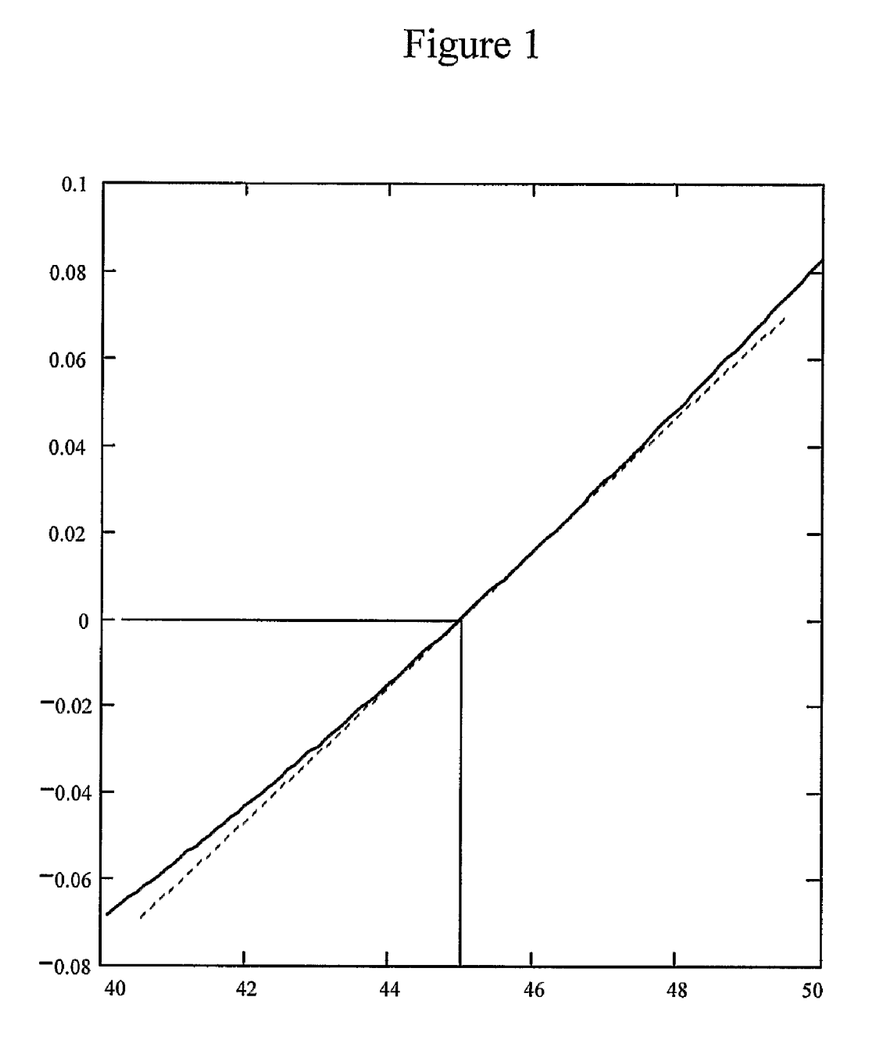
FIG. 1 shows a plot of absorbance versus optical rotation.

Consider two ideal polarizers, with no absorbance other than that produced by optical rotation, arranged so that their planes of polarization are at a 45° angle. According to Malus' law, in this situation, the intensity of light passing through the combination should be $$I° = k \cos^2 45° \tag{1}$$

where k is a constant of proportionality. If an optically active sample is placed between the polarizers, it will rotate the plane of polarization of the light incident on the second polarizer. Depending on the direction of the optical rotation, the light intensity may increase or decrease. Thus, when a transparent optically active sample such as sugar is placed between the polarizers, $$I = k \cos^2(45° \pm q) \tag{2}$$

where q is the optical rotation due to the presence of the chiral sample. The ± sign refers to the direction of the rotation (i.e., did the sample rotate the light so that the total angle (a) increased or decreased). According to Eqns. 1 and 2, the absorbance produced by the presence of the transparent optically active sample will be given by $$A = -\log(I/I°) = -\log\{(\cos^2 a)/0.50\} = -\log(2 \cos^2 a) \tag{3}$$

where a is 45°±q. FIG. 1 shows a plot of the absorbance A versus a as q varies between 0 and ±5° (a goes from 40° to 50°). From the plot, it can be seen that the absorbance produced by the optical rotation of the chiral sample varies nearly linearly with the optical rotation (q) itself. The preferred spectropolarimeter used in the current method makes use of this property.

Equation 3 will not apply if the chiral sample contains colored material that also produces an absorbance. This problem can be eliminated by careful background correction procedures described herein.

Figure 2:
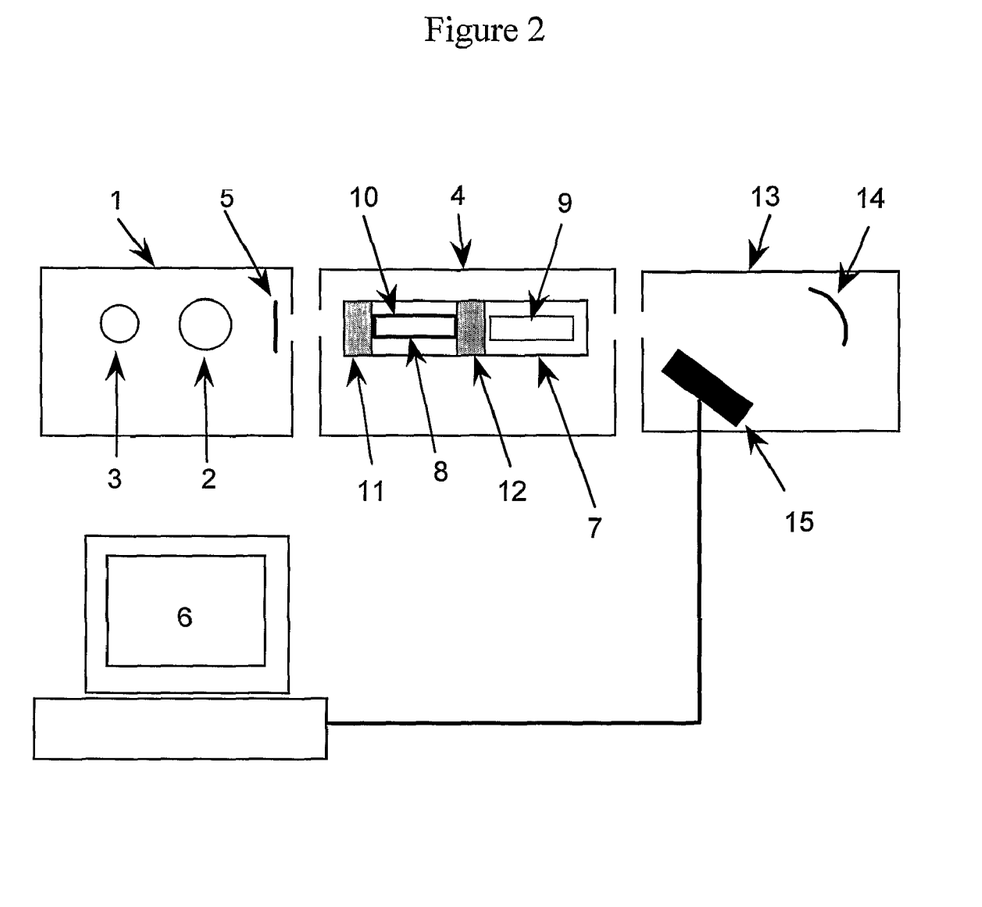
FIG. 2 shows a schematic diagram of an example of the spectropolarimeter.

A schematic diagram of a preferred embodiment of the spectropolarimeter is shown in FIG. 2. Housing 1 is a compartment for the light sources of the spectrometer. Lamp 2 is a low-pressure deuterium arc that produces light in the ultraviolet region of the spectrum. Lamp 3 is a quartz-halogen lamp that produces light in the visible and near-IR regions of the spectrum, thereby providing spectral coverage from 200-1100 nm. The long wavelength cutoff of the instrument is limited by the response of the solid-state array detector and not the radiant emission from the light sources. The lamps are arranged so that their radiation forms a single beam that passes into the sample compartment 4. The sample compartment 4 is made long enough to accommodate long pathlength cells, if needed. A shutter 5, operationally connected to the computer 6 allows light to pass from the lamp housing 1 for a predetermined exposure period when the spectrometer is activated. The sample compartment 4 contains a specially-designed sample holder 7 for the sample cell 8. The sample holder is made so that the sample can be uniformly and reproducibly placed in two locations 9 and 10. Also on the sample holder are two Glan-Taylor prism polarizers 11 and 12. These polarizers are fixed in the sample holder with their planes of polarization fixed at some predetermined angle (45°, for example). Following the sample holder is a polychromator 13 equipped with a concave holographic grating 14 and a solid-state array detector 15. The output from the solid-state array detector is operationally connected to the computer 6 to compute the absorbance spectrum of the assembly.

Figure 3:
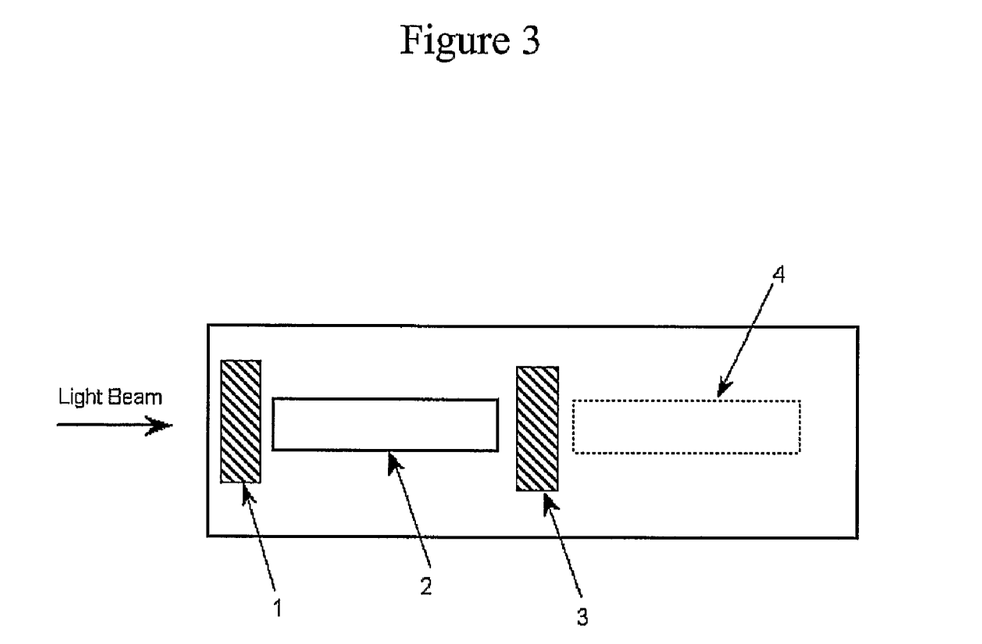
FIG. 3 shows a schematic view of the sample and prism holder of the example spectropolarimeter.

When the sample is placed in position 9 in the sample holder, it is after the pair of polarizers 11 and 12. This configuration corresponds to the orientation used to determine the blank for the sample and is also shown in FIG. 3. When the sample is in position 9 in the sample holder the measured absorbance spectrum 16 corresponds to the total absorbance produced (as a function of wavelength) by the polarizers 11 and 12 and any absorbance produced by any achiral components in the sample. When the sample is placed in position 10 of the sample holder, it is between the two polarizers, and a second absorbance spectrum 17 can be acquired with the instrument. When the sample is in this position, any chiral components in the sample will rotate the plane of polarized light by some amount determined by the specific rotation of the compound(s). This rotation will alter the amount of light that is able to pass through the pair of polarizers in accordance with Malus' law: $I = I° \cos^2 a$. Thus, the presence of a chiral compound or compounds in the sample will alter the amount of light emerging from polarizer 12, thereby altering the apparent absorbance. Since absorbances are additive, if the absorbance spectrum 16 is subtracted from absorbance spectrum 17, the difference absorbance spectrum 18 will be the absorbance as a function of wavelength due solely to the optical rotation caused by the presence of the chiral components in the sample, regardless of whether the sample is colored or not.

Because the instrument is a spectropolarimeter that determines optical activity as a function of wavelength, the entire spectrum (from 200-1100 nm) rather than a single wavelength can be used in the analytical procedure. To determine the concentration of an unknown chiral compound (like sugar), one would start by making a multivariate regression model using a series of calibration samples whose concentration (of sucrose, for example) is known. These samples can be made up gravimetrically in the laboratory using pure sucrose in water. Once the calibration samples have been prepared, their optical rotatory dispersion (ORD) spectra would be obtained (in absorbance) with the instrument. Once the multivariate regression model has been prepared with transparent sucrose solutions, unknown samples can be analyzed by obtaining their ORD spectra using the instrument. These ORD spectra (which are corrected for color) can then be input into the regression model to calculate the sucrose concentration of the unknown. Because the instrument corrects for color, samples of colored unknowns (like coffee or soft drinks) can be analyzed with the same multivariate regression model even if they contain components like citric acid (in soda) that are not present in the calibration samples.

Briefly, the current method for determining sucrose concentration has the following steps. First, a series of pure sucrose solutions are prepared with known concentrations. The spectral data of the known samples are collected with the samples placed to the right of the fixed polarizers, to measure the background absorbance of anything unrelated to optical rotation. These background absorbances are used as a baseline, or as the blank within the spectropolarimeter. Then the spectral data of the same known samples is collected again, with the samples placed between the polarizers. This spectral data is corrected to disregard the background absorbances. Using these colorless sucrose standards, a multivariate regression model is prepared that relates the measured absorbance due to the optical rotation of sucrose to the concentration. To analyze a colored sucrose solution, the blank spectrum of the solution is first recorded by placing the sample in the position that is after the polarizers. Then, the sample is placed between the polarizers and the color-corrected spectrum is recorded. This spectral data is input into the regression model to predict the sucrose concentration of the colored solution.

Example 1

Instrumentation and Testing of Spectropolarimeter

A Hewlett Packard-Agilent 8453 UV-visible spectroscopy system (Palo Alto, Calif.) was modified to extend its mode of operation as a NIR spectropolarimeter. A spectropolarimeter is a polarimeter that operates over a continuous range of wavelengths. In the present case the range comprised the near infrared region (NIR) of the electromagnetic spectrum. To achieve this modification, a new base was built to fit the optical path. This base was used both as a cell and prism holder. Two Glan-Taylor prisms were fixed at an angle of 45° and at a distance of 20 mm from one another, which corresponds to the length of the cell used. A schematic view of the set up is shown in FIG. 1.

The behavior of the instrument as a spectropolarimeter was tested using seven 20% by mass sucrose solutions prepared from reagent grade sucrose (Mallinckrodt Chemicals, Hazelwood, Mo.). These solutions were colorless. The 20% m/m sucrose solutions were prepared by direct dilution of the proper amount of sucrose, allowed to settle for 30 minutes and measured to record the optical rotatory dispersion ("ORD"), i.e. the variation of the angle of rotation with wavelength, of the sucrose at 365, 405, 435, 546, 589 and 633 μm. These wavelengths are predetermined in the polarimeter (Autopol III®, Rudolph Research Analytical, Hackettstown, N.J.).

Figure 4:
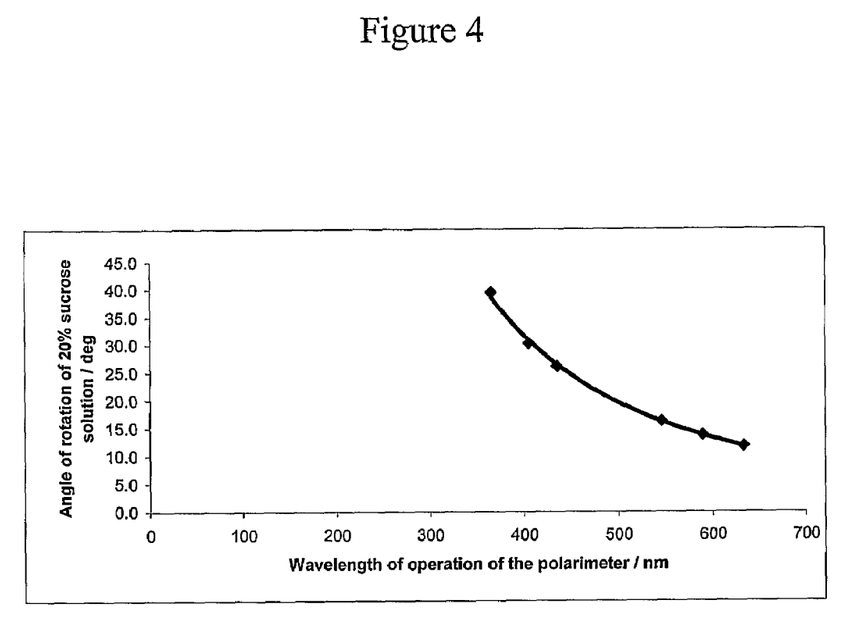
FIG. 4 shows an optical rotatory dispersion ("ORD") curve corresponding to the variation of the angle of optical rotation with wavelength for 20% m/m sucrose solutions.

The angle of rotation was recorded for each solution at the mentioned wavelengths. The average angle of rotation (n=7 replicates of 20% sucrose solution) was calculated for each wavelength and plotted against the correspondent wavelength to obtain the ORD. FIG. 4 shows the results.

The same solutions were measured in the spectrophotometric system with the polarizer instrumentation, as describe above. These measurements were taken the same day as the polarimetric measurements. The absorbance spectrum of each solution was taken. From each spectrum, the absorbances corresponding to those at the wavelengths of the polarimeter were taken. The average absorbance of the solutions at each corresponding wavelength was plotted against wavelength, obtaining an ORD equivalent, similar to the polarimetric one. The results are shown in FIG. 5.

Figure 5:
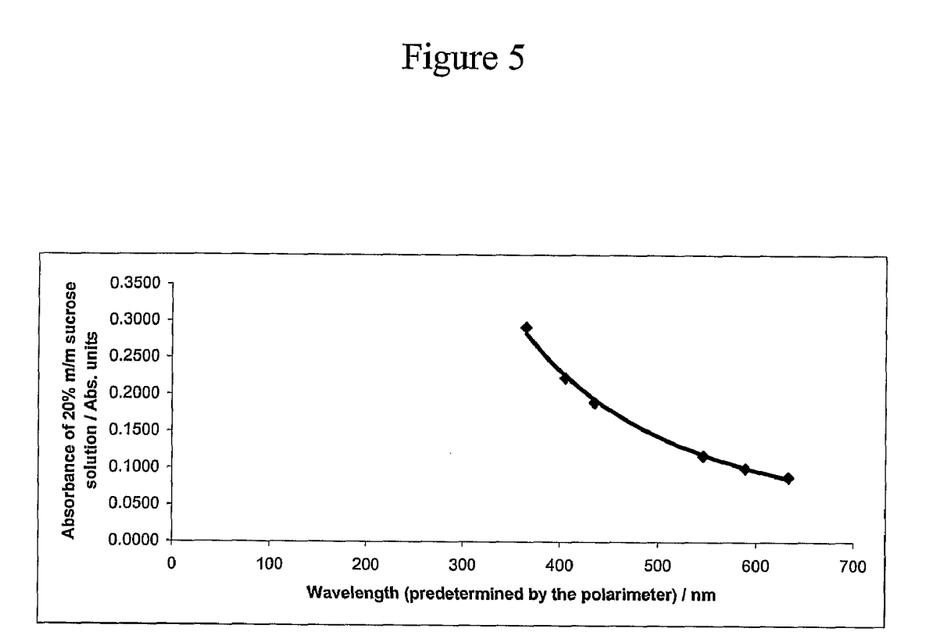
FIG. 5 shows an ORD equivalent corresponding to the variation of the absorbance with wavelength for 20% m/m sucrose solutions determined using the example spectropolarimeter.
Figure 6:
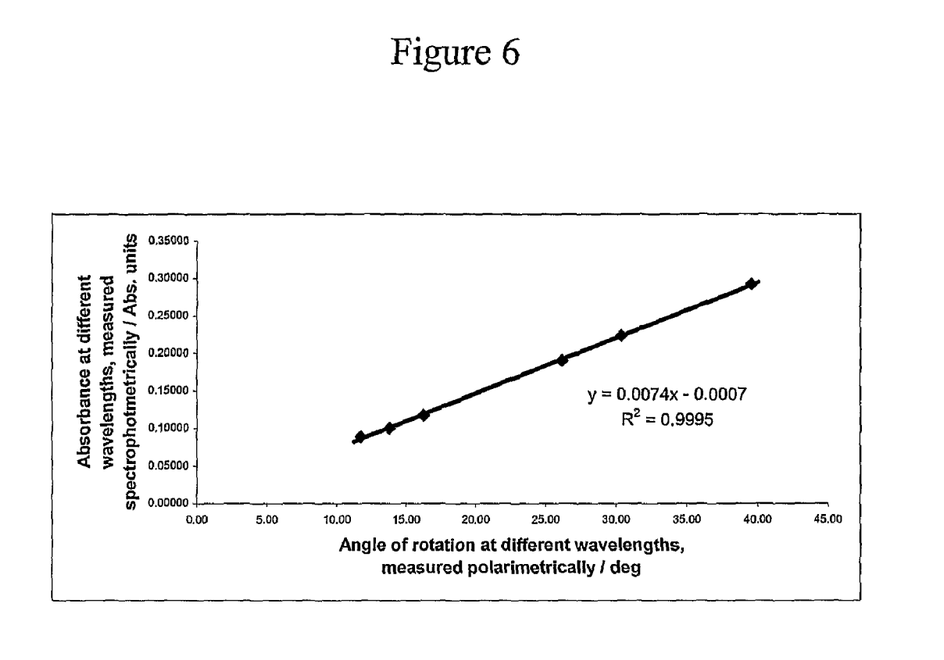
FIG. 6 shows a plot of the absorbance values obtained with the example spectropolarimeter against the measured angle of rotation determined using conventional polarimetry.

As can be seen from FIGS. 4 and 5, measurements done with the new instrument are equivalent to those obtained using conventional polarimetry. Further correspondence in the measurements for solutions 20% m/m in sucrose is evident from FIG. 6. This figure indicates a linear relation between the angle of rotation and the absorbance values recorded with the new instrument. Again, each point in the figure correspond to each of the wavelengths at which is possible to use the polarimeter.

Figure 7:
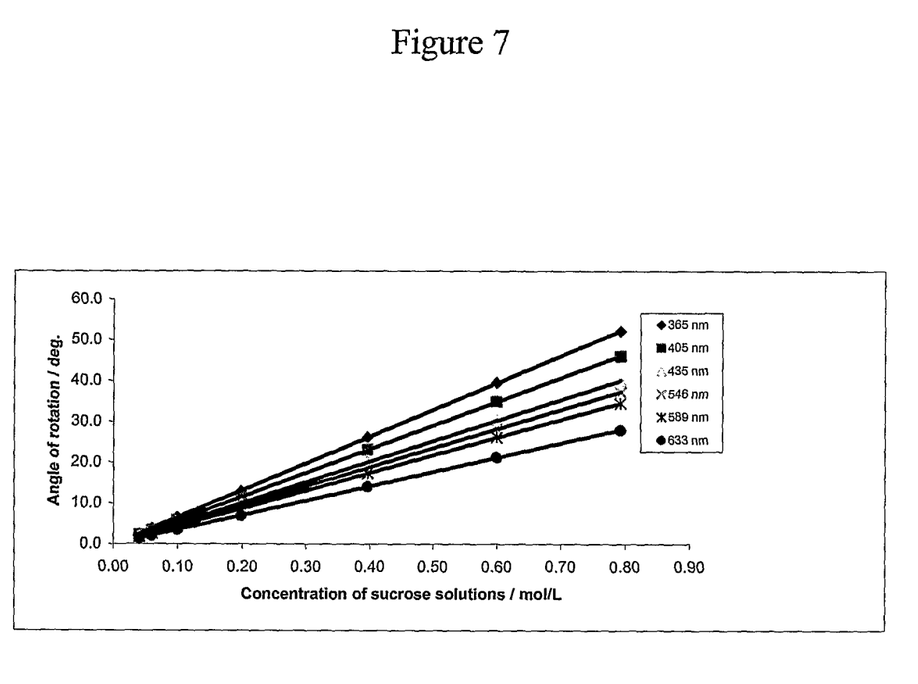
FIG. 7 shows the angle of rotation versus the concentration of sucrose at six different wavelengths for aqueous sucrose solutions using conventional polarimetry.

An additional set of solutions was prepared to observe the behavior of the spectropolarimetric system over a range of concentrations. A 34% m/m stock solution of reagent-grade sucrose (Mallinckrodt) was prepared by direct dilution of the proper amount of sucrose to 500 mL, and let to settle for 30 minutes. After that period, aliquots of 2, 3, 5, 10, 20, 30 and 40 mL were taken and diluted to a final volume of 50 mL each, with deionized water. Solutions were left to settle for other 30 minutes. After that period, the angle of rotation was measured at 365, 405, 435, 546, 589 and 633 nm in the polarimeter, and the absorbance spectrum recorded in the new NIR spectropolarimeter. Two plots were built: for the polarimetric system, a plot of angle of rotation vs. concentration at each wavelength is shown in FIG. 7. For the spectropolarimeter, absorbance vs. concentration at each wavelength appears in FIG. 8.

Figure 8:
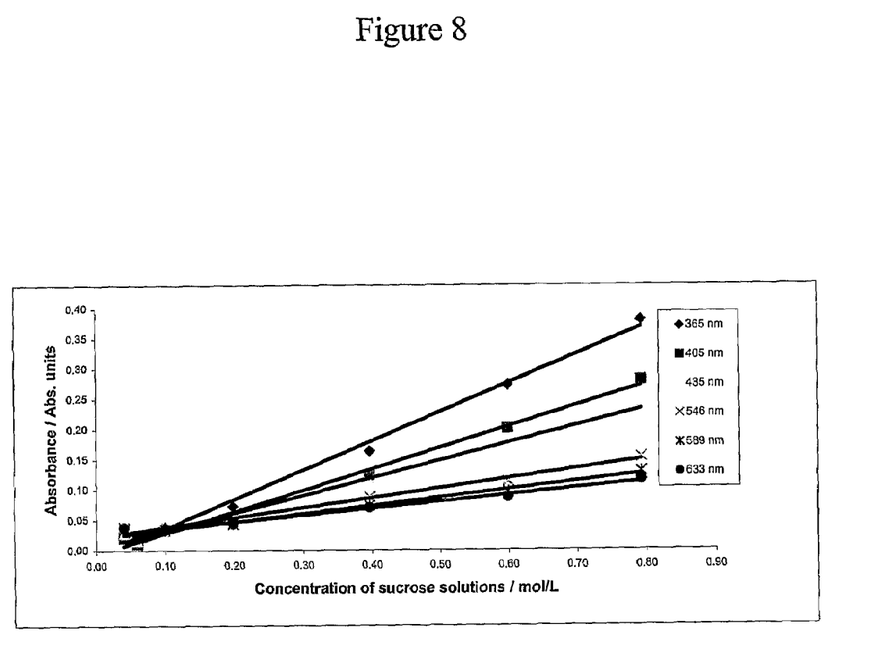
FIG. 8 shows absorbance versus concentration of sucrose at six different wavelengths for aqueous sucrose solutions using the example spectropolarimeter.

In FIG. 7, each line shows the increase in angle of rotation as the concentration of sucrose increases, at each corresponding wavelength. Also it is observed that longer wavelengths show lines with smaller slopes. This confirms the result from FIG. 4 showing smaller angles of rotation as wavelength increases. The same trend is shown in FIG. 8 for the spectropolarimeter.

Figure 9:
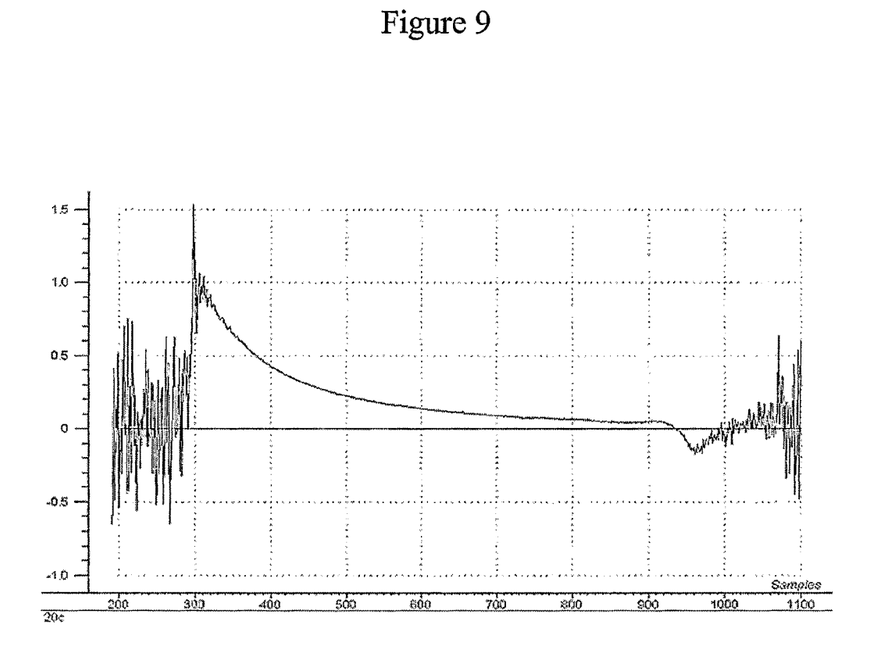
FIG. 9 shows an ORD like spectrum for a 20% sucrose solution, using the example spectropolarimeter.

The ORD type spectrum of a 20% sucrose solution is shown in FIG. 9. In general, the spectropolarimeter is capable of recording absorbances from about 350 nm to 950 nm. Using Glan-Taylor polarizers this can be extended to 250-950 nm. The "noisy" signals out of this range are due to the absorbance of the polarizers themselves. The region between 750 nm to 950 nm can be used in the study of colored absorbing substances capable of interaction with polarized light, such as sugars.

Example 2

Prediction of Sucrose Concentration in Unknown Samples

A calibration set of samples was prepared using reagent grade sucrose (Mallinckrodt). A 5% stock solution was prepared by diluting 25 g of sucrose in 500 mL of deionized water. From this solution, aliquots of 1, 2, 3, 4, 5, 6, 7, 8, 9, 10, 11 and 12 mL were taken and diluted to a final volume of 15 mL. Three replicates of each solution were prepared, giving 36 colorless solutions for the model. Data was analyzed and the model for predictions was built by partial least squares regression ("PLS1") with a commercial chemometric software package ((Unscrambler™, CAMO, Inc., Corvallis, Oreg.).

Three commercially available types of sugars were used to test the sample: raw sugar, light brown sugar and dark brown sugar. Another sample was prepared by mixing with coffee. The first three samples were prepared directly by dissolving approximately 2.5 g of sugar in 50.00 mL of deionized water. From this solutions, aliquots of 5 mL were taken and diluted to 15 mL, to prepare 7 replicates. The sample of coffee was prepared by measuring 2.5 g of reagent grade sucrose and 0.2 g of instant coffee, and diluting to 50 mL. Aliquots of 5 mL were taken and diluted to a final volume of 15 mL. 7 replicates were also prepared.

All solutions, both the calibration set and the unknown samples, were measured with background correction. The polarization system allowed for appropriate corrections for colored solutions, as shown in FIG. 3. In FIG. 3, the source of light is at the left in the scheme. When the cell was placed in position 4, the instrument recorded a blank spectrum. In this position, sucrose, or any other analyte capable of rotating the plane of polarization of polarized light, does not induce any rotational change that can be detected because there is no polarizer at the end of position 4. Once this correction was done, the cell was changed manually from position 4 to position 2. A new spectrum was recorded keeping the previous blank correction. When the cell was in position 2, light was polarized by prism 1, and this polarized light's plane of polarization was rotated by sucrose. This rotation made the polarized light reach prism 3 (which is fixed at an angle of 45° with respect to 1) at an angle different from that without the sugar, so the absorbance was increased with respect to the blank directly proportional to concentration. The procedure of blank correction and sample recording was repeated for each solution, regardless of it being colored or colorless.

Figure 10:
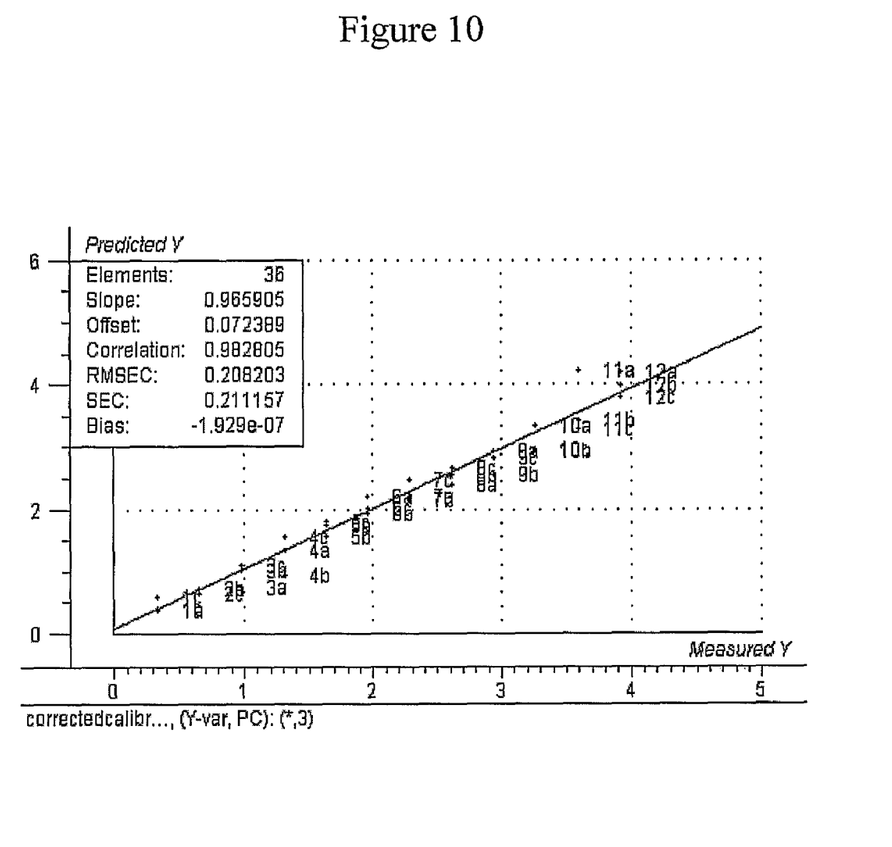
FIG. 10 shows a multivariate regression plot for a calibration set of sugar samples.

In the model built with pure sucrose, colorless solutions were measured with the described blank correction. The sample set included 36 solutions at twelve concentration levels. A multivariate regression, i.e. a statistical regression for predictions over a range of wavelengths instead of just one wavelength, was made by partial least squares fitting (PLS). The regression line is shown in FIG. 10. The wavelength range was from 750 nm to 950 nm.

In the upper left square it can be seen that there were 36 elements fitted. The slope is close to 1, which accounts for the fact that the predicted values of sucrose concentrations are statistically equivalent to the standard concentrations used to build the model. The offset is close to 0, and the correlation is close to 1, which is ideal. The other parameters refer to the error of prediction, which is low.

Figure 11:
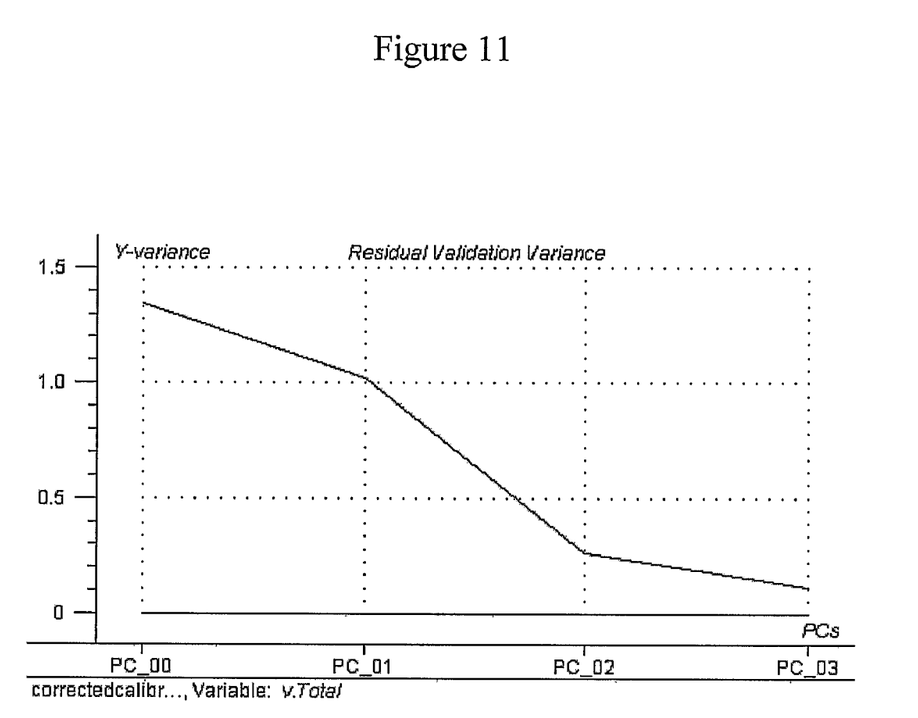
FIG. 11 shows the unexplained variance as a function of the number of PLS components in the model for predicting sugar concentration.

FIG. 11 is a representation of the unexplained variability of the data. This shows how well the model is working to make predictions with respect to the number of PLS components. The result is that 3 components explain most of the variation. If the program is commanded to use more than 3, over-fitting will occur, and this will decrease the capability to obtain reliable predictions.

Figure 12:
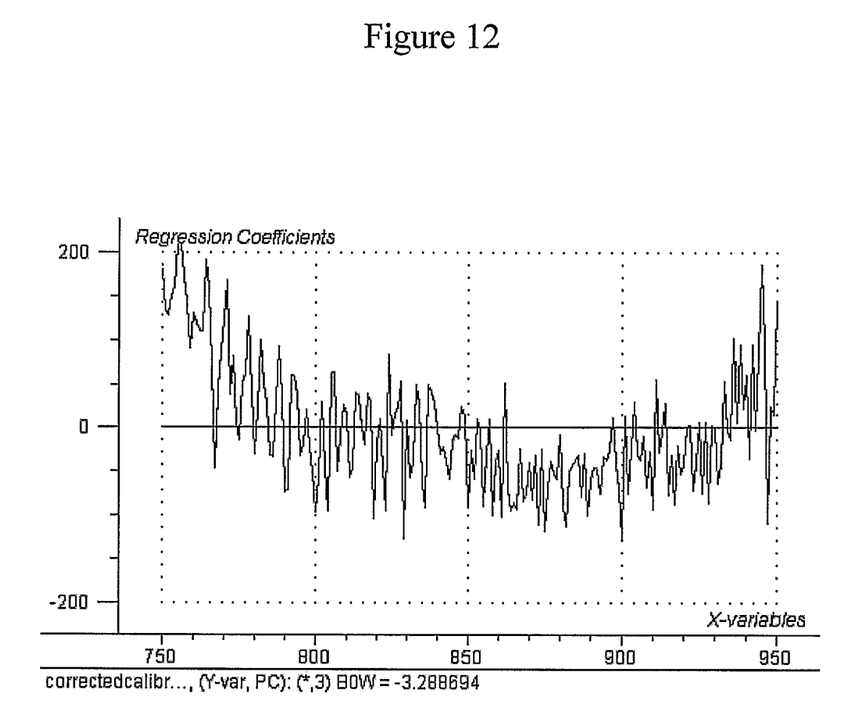
FIG. 12 shows the regression model coefficients for predicting sugar concentration as a function of wavelength.

In FIG. 12 it is specified that the regression was made over a range of 200 wavelengths. A multivariate regression implies that the model is a weighted average of several univariate regressions, 200 in this case. FIG. 12 actually shows the model, or the regression vector, used to predict future unknown samples.

Figure 13:
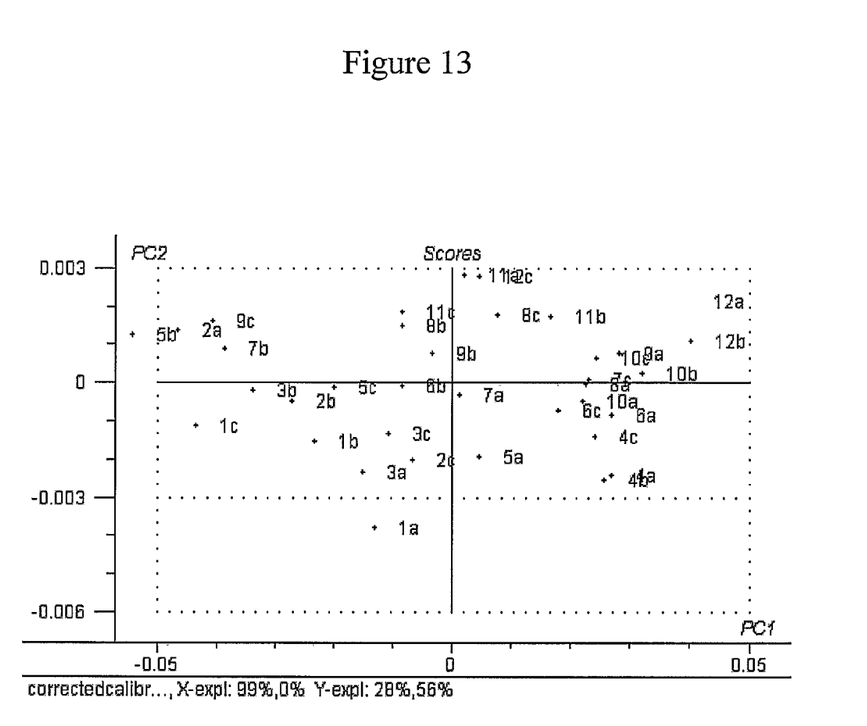
FIG. 13 shows a scores plot for the model for predicting sugar concentration for the first two PLS components that explain 84% of the Y-variance.

FIG. 13 shows a scores plot for the 36 samples used to make the model. In this plot, the samples are plotted on the new coordinate system composed of PLS components. The first two PLS components explain 84% of the concentration information. There are no obvious groupings among the samples.

The four unknown sugar samples were measured using NIR spectropolarimetry, as described above, and their predicted percentages of sucrose were calculated using the regression model. The results are shown in Table 1 below.

TABLE 1

| Sample | Predicted percentage | Reference percentage |
|---|---|---|
| Sugar in the raw | 92.22 | 90-97 |
| Light brown sugar | 89.53 | 85-90 |
| Dark brown sugar | 117.55 | 85 |
| Coffee | 106.48 | 90 |

The predicted percentage is the percentage of sucrose present in each sample as predicted with the regression model developed with colorless solutions. The reference percentage refers to the actual percentage of sucrose in each sample as reported in the literature for each product by the manufacturer.

For raw sugar and light brown sugar, the predicted percentage is within the range reported. Dark brown sugar gives a higher result than that expected because of the additional presence of inverted sugar, which increases the amount of glucose and fructose. Both of these other sugars are also optically active, but they were not considered in the model. Coffee also gives a higher prediction. This sample was prepared using pure sucrose and adding coffee as an interference. Since coffee itself contains sucrose from the roasting process, it was expected to obtain an increased prediction, which is reasonable.

REFERENCES CITED

The entire content of each of the following documents is hereby incorporated by reference.

OTHER PUBLICATIONS

Yamamoto, et al., *Spectroscopy*, vol. 16, pp. 24-33, 2001

What is claimed is:
1. A method for determining an unknown sugar concentration in an unknown sample, comprising:
   collecting unknown background spectral data of an unknown sample by passing light of various wavelengths through a first polarizer, a second polarizer oriented at a 45 degree angle with respect to the first polarizer, and the unknown sample, and recording the resultant light intensity with a spectrometer to give the unknown background spectral data;
   collecting unknown spectral data of the unknown sample by passing light of the various wavelengths through the first polarizer, the unknown sample, and the second polarizer oriented at a 45 degree angle with respect to the first polarizer, and recording the resultant light intensity with the spectrometer to give the unknown spectral data;

adjusting the unknown spectral data by subtracting the unknown background spectral data to give adjusted unknown spectral data; and inserting the adjusted unknown spectral data into a regression model to allow calculation of the unknown sugar concentration in the unknown sample.

2. The method of claim 1, wherein the regression model is created by:

preparing a series of known samples, each of the known samples comprising a sugar compound having a known concentration;

collecting background spectral data of the known samples by passing light of various wavelengths through a first polarizer, a second polarizer oriented at a 45 degree angle with respect to the first polarizer, and the known sample, and recording the resultant light intensity with a spectrometer to give the background spectral data;

collecting known spectral data of the known samples by passing light of the various wavelengths through the first polarizer, the known sample, and the second polarizer oriented at a 45 degree angle with respect to the first polarizer, and recording the resultant light intensity with the spectrometer to give the known spectral data;

adjusting the known spectral data by subtracting the background spectral data to give adjusted known spectral data; and performing a principal component analysis and a regression of the adjusted known spectral data for each of the known samples to create the regression model.

3. The method of claim 1, wherein the sugar is sucrose.

4. The method of claim 1, wherein the spectral data is UV spectral data comprising the near infrared region.

5. A method for determining an unknown sugar concentration in an unknown sample, comprising:

preparing a series of known samples, each of the known samples comprising a sugar compound having a known concentration;

collecting background spectral data of the known samples by passing light of various wavelengths through a first polarizer, a second polarizer oriented at a 45 degree angle with respect to the first polarizer, and the known sample, and recording the resultant light intensity with a spectrometer to give the background spectral data;

collecting known spectral data of the known samples by passing light of the various wavelengths through the first polarizer, the known sample, and the second polarizer oriented at a 45 degree angle with respect to the first polarizer, and recording the resultant light intensity with the spectrometer to give the known spectral data;

adjusting the known spectral data by subtracting the background spectral data to give adjusted known spectral data;

performing a principal component analysis and a regression of the adjusted known spectral data for each of the known samples to create a regression model;

collecting unknown background spectral data of an unknown sample by passing light of the various wavelengths through a first polarizer, a second polarizer oriented at a 45 degree angle with respect to the first polarizer, and the unknown sample, and recording the resultant light intensity with a spectrometer to give the unknown background spectral data;

collecting unknown spectral data of the unknown sample by passing light of the various wavelengths through the first polarizer, the unknown sample, and the second polarizer oriented at a 45 degree angle with respect to the first polarizer, and recording the resultant light intensity with the spectrometer to give the unknown spectral data;

adjusting the unknown spectral data by subtracting the unknown background spectral data to give adjusted unknown spectral data; and inserting the adjusted unknown spectral data into the regression model to allow calculation of the unknown sugar concentration in the unknown sample.

6. The method of claim 5, wherein the sugar is sucrose.

7. The method of claim 5, wherein the spectral data is UV spectral data comprising the near infrared region.

* * * * *